(12) United States Patent
Skelton

(10) Patent No.: US 10,806,818 B2
(45) Date of Patent: Oct. 20, 2020

(54) METHOD OF TREATING AIR PASSING THROUGH AN AIR HANDLING UNIT

(71) Applicant: PetAirapy LLC, St. Charles, IL (US)

(72) Inventor: David Skelton, Bartlett, TN (US)

(73) Assignee: Petairapy LLC, St. Charles, IL (US)

( * ) Notice: Subject to any disclaimer, the term of this patent is extended or adjusted under 35 U.S.C. 154(b) by 279 days.

(21) Appl. No.: 15/969,367

(22) Filed: May 2, 2018

(65) Prior Publication Data

US 2019/0275189 A1 Sep. 12, 2019

Related U.S. Application Data

(60) Provisional application No. 62/641,787, filed on Mar. 12, 2018.

(51) Int. Cl.
| | |
|---|---|
| *H01R 43/00* | (2006.01) |
| *A61L 9/20* | (2006.01) |
| *F21V 23/06* | (2006.01) |
| *F21V 33/00* | (2006.01) |
| *F21V 19/00* | (2006.01) |
| *F21V 23/02* | (2006.01) |

(52) U.S. Cl.
CPC ............... *A61L 9/20* (2013.01); *F21V 19/00* (2013.01); *F21V 23/02* (2013.01); *F21V 23/06* (2013.01); *F21V 33/0096* (2013.01); *A61L 2209/12* (2013.01); *Y10T 29/49169* (2015.01)

(58) Field of Classification Search
USPC ................................ 29/854, 428, 592.1, 825
See application file for complete search history.

(56) References Cited

U.S. PATENT DOCUMENTS

| | | | | |
|---|---|---|---|---|
| 6,855,295 | B2* | 2/2005 | Kulp | F24F 3/16 |
| | | | | 422/121 |
| 7,385,204 | B2* | 6/2008 | Bircher | A61L 9/20 |
| | | | | 250/453.11 |
| 8,388,731 | B2* | 3/2013 | Metteer | A61L 9/02 |
| | | | | 95/3 |

* cited by examiner

*Primary Examiner* — Thiem D Phan
(74) *Attorney, Agent, or Firm* — Wood, Phillips, Katz, Clark & Mortimer

(57) ABSTRACT

A method of treating air passing through an air handling unit having a housing extending around an air handling space and a primary air treatment system that treats air as the air passes through the air handling unit between air inlet and outlet locations on the air handling unit. First and second fixtures are obtained, each having a housing and a UV light source. The first and second fixtures are strategically mounted to the air handling unit so that UV light from each of the UV light sources on the first and second fixtures treats air moving through the air handling unit with the UV light sources on the first and second fixtures energized. The first and second fixtures are serially electrically connected to a power source to thereby cause the UV light sources on the first and second fixtures to be energized through the power source.

21 Claims, 4 Drawing Sheets

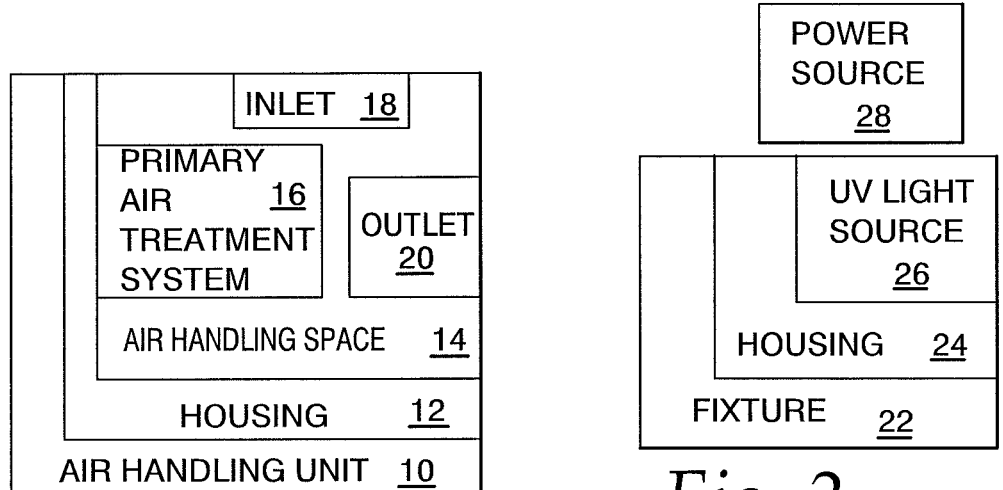
Fig. 1 (PRIOR ART)
Fig. 2
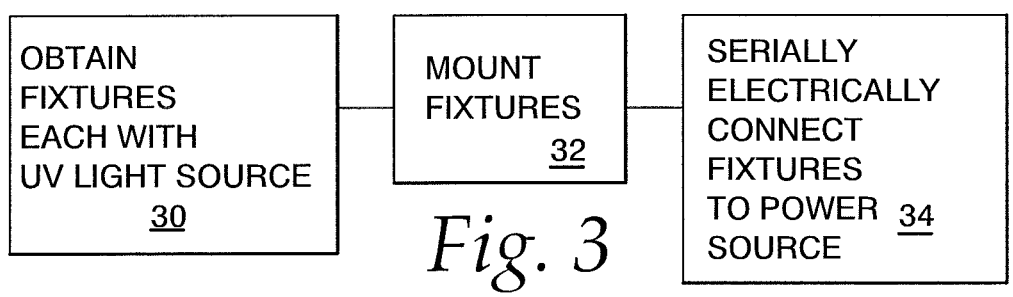
Fig. 3
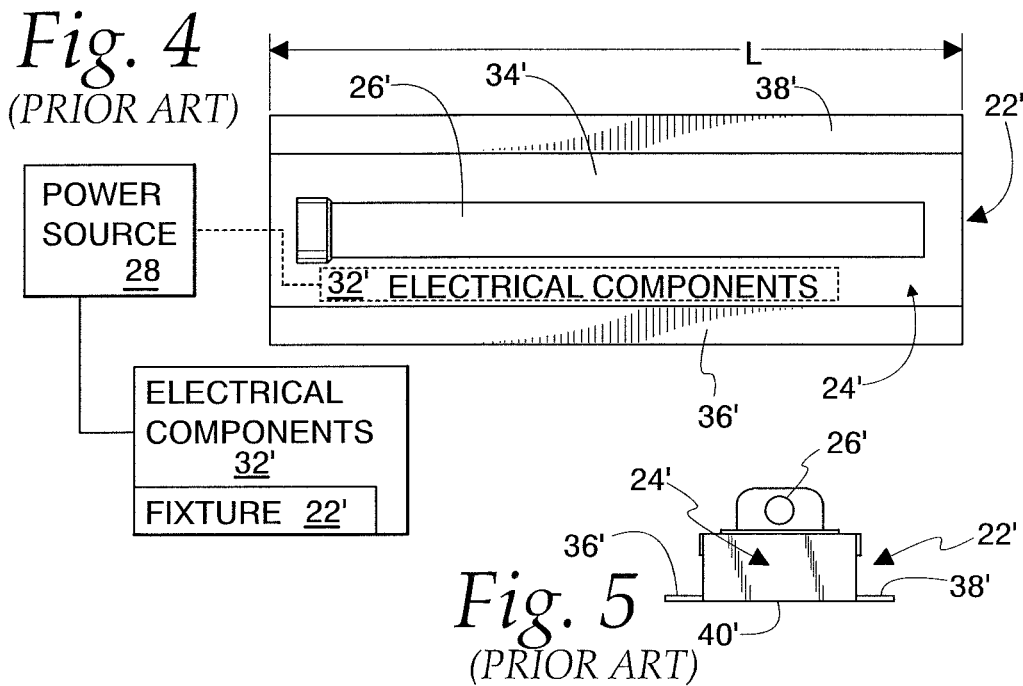
Fig. 4 (PRIOR ART)
Fig. 5 (PRIOR ART)

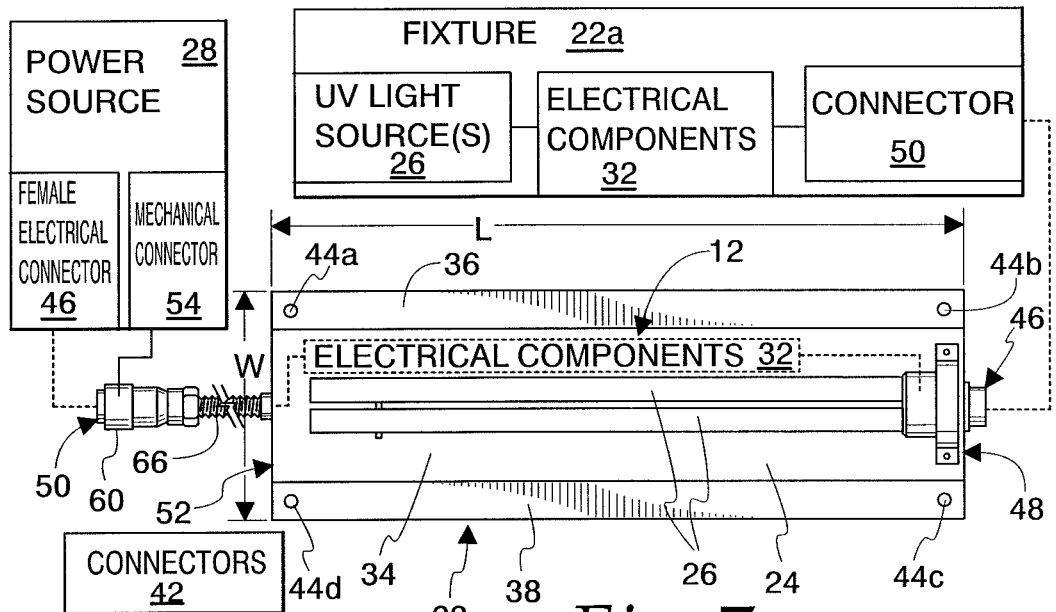
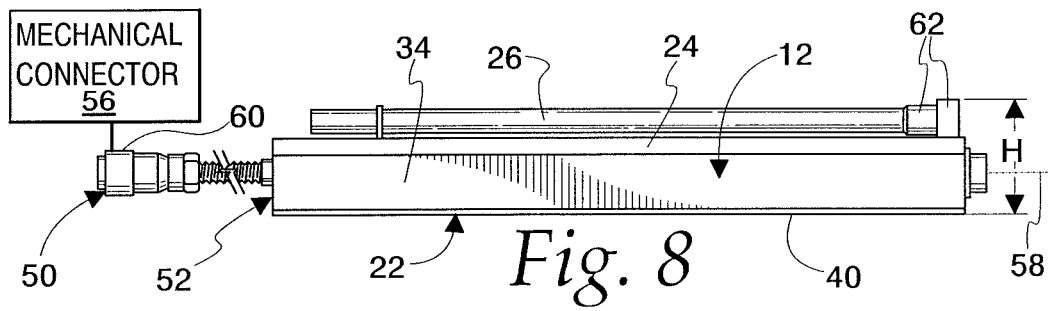
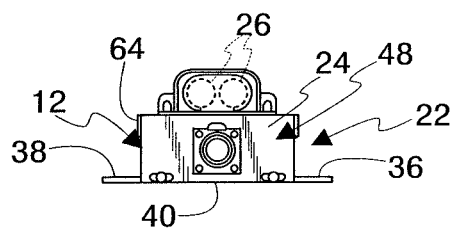

METHOD OF TREATING AIR PASSING THROUGH AN AIR HANDLING UNIT

BACKGROUND OF THE INVENTION

Field of the Invention

This invention relates to air handlers through which air is advanced as it is conditioned before introduction into a space and, more particularly, to a method of treating the advancing air with germicidal UV light.

Background Art

It is known to treat air advancing through air handling units with UV light to kill or deactivate airborne molds, spores, viruses, and other pathogens (collectively, "germs"), that may have adverse effects on the health of humans and/or their pets that occupy a space within which the air is introduced. Air handlers may be installed on roofs or interiorly of building structures and have many different capacities/sizes and shapes.

UV light units are commonly placed strategically within an air passage bounded by a housing on the air handling unit. The air advancing through the handling unit is caused to pass through the generated light, as an incident of which the targeted germs are deactivated or killed. Effective treatment of the air requires that substantially all of the air moving through the air handling unit be exposed to the UV light energy and that the intensity of that light be adequate to effect the desired germicidal sanitation.

To meet the anticipated range of product demands for full exposure of air moving through an air handler to a desired level of UV light energy, manufacturers offer a range of different light unit configurations. For example, the units and associated bulbs may have different lengths. Units are offered with different numbers of bulbs. Thus, installers will select units particularly suited to the size and configuration of the particular air handling unit that they are working on.

In some applications, there is an extended passage cross section or length bounded by an air handler housing. It is desirable to expose substantially the whole volume of air residing in the air handling unit at any point in time to a high level of UV light energy to maximize effectiveness. This may necessitate the use of multiple units. Since the conventional light units are self-contained, they must be separately wired from a power source to the particular location at which they reside, once installed. In relatively large air handling units in which high energy light treatment is desired, several UV light units may be required to be individually wired directly to the power source. This may result in a maze of wires that complicates installation, particularly in a limited volume of space that may be available within the air handler unit and which is occupied in part by other air treatment components.

Because the standard in the industry has been to use self-contained standard UV light generating units, customized installation often becomes complicated. Consumers may opt to avoid the expense of customization and use the standard units in a manner that does not treat the air with UV light to an extent that is optimal. The industry continues to seek out better designs that allow systems to be efficiently installed while effecting exposure of an adequate air volume to a desired level of UV light energy.

SUMMARY OF THE INVENTION

In one form, the invention is directed to a method of treating air passing through an air handling unit. The air handling unit has a housing extending around an air handling space. A primary air treatment system treats air as the air passes through the air handling unit between air inlet and outlet locations on the air handling unit. The method includes the steps of: obtaining first and second fixtures each having a housing and a UV light source; strategically mounting the first and second fixtures to the air handling unit so that UV light from each of the UV light sources on the first and second fixtures treats air moving through the air handling unit with the UV light sources on the first and second fixtures energized; and serially electrically connecting the first and second fixtures to a power source to thereby cause the UV light sources on the first and second fixtures to be energized through the power source.

In one form, the first and second fixtures are substantially the same.

In one form, the first fixture has electrical input and output connectors. One of the electrical input and output connectors is connected to the housing on the first fixture through a flexible whip.

In one form, the second fixture has an electrical input connector. The electrical output connector on the first fixture and electrical input connector are configured to be press connected, each to the other.

In one form, there are cooperating holding connectors on the first and second fixtures that maintain the press connected electrical input connector on the second fixture and electrical output connector on the first fixture together.

In one form, the cooperating holding connectors are configured to be engaged by moving the cooperating holding connectors relative to each other around an axis.

In one form, the cooperating holding connectors are configured to be threadably engaged with each other.

In one form, the flexible whip is an MC cable.

In one form, the electrical input connector on the first fixture is connected to the housing through the flexible whip.

In one form, there are electrical and mechanical connectors associated with the power source that respectively cooperate with electrical and mechanical connectors on the first fixture. The electrical and mechanical connectors associated with the power source and on the first fixture are configured to allow the electrical and mechanical connectors associated with the power source and on the first fixture to be releasably maintained together.

In one form, the flexible whip has a length of at least one foot.

In one form, the flexible whip has a length of at least 2 feet.

In one form, the first and second fixtures are substantially the same.

In one form, the housings on the first and second fixtures are substantially the same and have an elongate shape with a lengthwise axis.

In one form, the first and second fixtures are mounted to the air handling unit housing so that the lengthwise axes of the housings of the first and second fixtures are substantially parallel.

In one form, the first and second fixtures are mounted to the air handling unit housing so that the axes of the housings of the first and second fixtures are angled with respect to each other.

In one form, the first and second fixtures are mounted to the air handling unit housing so that the axes of the housings of the first and second fixtures reside in corresponding planes that are not coincident and are not parallel.

In one form, the first and second fixtures are mounted to the air handling unit housing so that the axes of the housings of the first and second fixtures reside in corresponding planes that are substantially orthogonal with respect to each other.

In one form, the primary treatment system is configured to at least one of: a) change a temperature of: b) humidify; c) clean; and d) move air moving within the air handling space.

In one form, the light source on each of the first and second fixtures includes multiple bulbs.

In one form, the method further includes a third fixture. The first, second, and third fixtures are serially connected, each to one of the power source and another of the fixtures.

BRIEF DESCRIPTION OF THE DRAWINGS

FIG. 1 is a schematic representation of an air handling unit of the type to which the invention is adapted;

FIG. 2 is a schematic representation of a fixture with a UV light source, according to the invention;

FIG. 3 is a flow diagram representation of a method of treating air passing through an air handling unit according to the invention;

FIG. 4 is a partially schematic, plan view of separate prior art fixtures, each with a UV light source;

FIG. 5 is an end elevation view of one of the fixtures in FIG. 4;

FIG. 6 is a schematic representation showing two of the inventive fixtures electrically connected in series to a power source;

FIG. 7 is a partially schematic, plan view of two fixtures with UV light sources, connected to each other and a power source, according to the invention;

FIG. 8 is a side elevation view of one of the fixtures in FIG. 7;

FIG. 9 is an end elevation view of the fixture in FIGS. 7 and 8;

DETAILED DESCRIPTION OF THE PREFERRED EMBODIMENT

Figure 10:
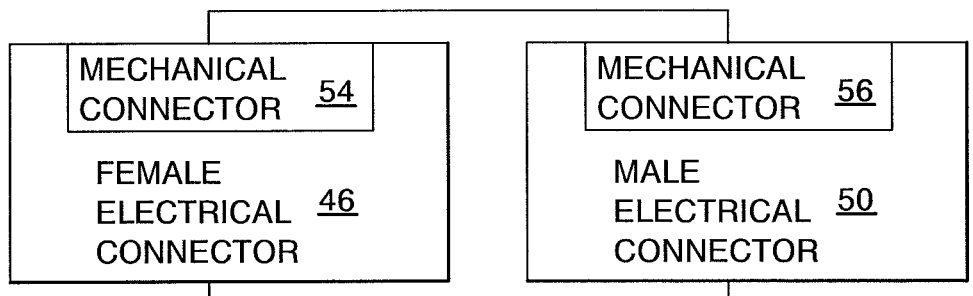
FIG. 10 is a schematic representation of electrical and mechanical fasteners usable to connect between the power source and a fixture and adjacent fixtures.

The invention is directed to a method of treating air passing through an air handling unit of the type shown generically at 10 in FIG. 1. The air handling unit 10 has a housing 12 extending around an air handling space 14. A primary air treatment system 16 treats air as it passes through the air handling unit 10 between air inlet and outlet locations 18, 20, respectively. The air handing unit 10 is shown generically and in this form is intended to encompass any type of unit that circulates, cleans, changes the temperature of, changes the humidity of, mixes, etc. air that is to be introduced into a space. Any type of unit that by treating the air changes its temperature, humidity, cleanliness, etc., or simply effects its movement within a space, is contemplated. Further, the primary air treatment system 16 that is responsible primarily for this air treatment may have, among other components, one or more fans that facilitate this treatment and induce flow of air between the inlet 18 and outlet 20.

The invention contemplates incorporating fixtures, each with a construction as shown generically at 22 in FIG. 2. Each fixture 22 has a housing 24 upon which a UV light source 26 is supported. The UV light source 26 is energized by an electrical power source 28.

Again, the generic showing of the fixture 22 is intended to encompass virtually all different types of UV light fixtures that can be used to generate UV light that has a sanitizing effect on the air which is exposed thereto.

The invention is directed principally to a method of treating air passing through the air handling unit 10. As shown in flow diagram form in FIG. 3, multiple fixtures 22 are obtained, as shown at block 30.

As shown at block 32, the multiple fixtures 22 are strategically mounted in relationship to the air handling unit 10 so that UV light from each of the UV light sources 26 on the fixtures 22 treats air moving through the air handling unit 10 with the UV light sources energized through the power source 28.

At least first and second of the fixtures 22 are serially electrically connected to the power source 28 to thereby cause the UV light sources 26 to be energized through the power source 28.

In FIGS. 4 and 5, a representative prior art fixture is shown at 22'. The fixture 22' has a housing 24' that contains electrical components 32' through which power from the source 28 is delivered to energize a UV light source/bulb 26'.

The housing 24' has a generally squared main portion 34' which defines a space for the electrical components 32' which may include, for example, a ballast, etc. Outturned flanges 36', 38' define, by themselves or in conjunction with the main housing portion 34' a generally planar mounting surface 40' that can be placed against a support surface and suitably secured thereto, as by conventional fasteners that might extend through the flanges 36', 38' or be otherwise configured to effect securement.

As noted in the Background portion hereinabove, the conventional fixtures 22' are made with different lengths L to emit sanitizing UV over an adequate dimension of a volume of air being treated. Further, multiple light sources/bulbs 26' might be provided on each unit to provide a higher level of UV light energy.

However, given the multiple configurations for air handling units, and their different dimensions, it is common to install multiple fixtures 22' to assure that the exiting air volume is adequately treated.

To accomplish this, each of the fixtures 22' is independently hardwired from the power source 28. While two fixtures 22' are shown, any number in excess of two might also be installed.

Thus, the installer is given the challenging task of cutting wires to appropriate length to individually electrically connect each of the light sources 26' directly to the power source 28. This may be particularly difficult in tight spaces where components of the primary air treatment system 16 occupy a substantial portion of that space and/or interfere with mounting of the fixtures 22' in optimal locations.

According to the invention, as shown in FIG. 6, multiple fixtures, in this case exemplary fixtures 22a, 22b, are serially electrically connected to the power source 28.

One specific, but not limiting, form of fixture 22, that facilitates the in-series construction, is shown in FIGS. 7-9. The fixture 22 has a housing 12 similar to that for the prior art fixture 22'. That is, the housing 12 has a squared main portion 34 with outturned flanges 36, 38. A flat mounting surface 40 facilitates placement against a substantially flat surface on the air handling unit housing 12. When so placed, fasteners 42 can be directed through one or more openings 44a, 44b, 44c, 44d and into the housing 12 to effect securement.

However, the fixtures 22 can be supported in any other manner, and in other orientations relative to a support surface, and using any other type of securement structure. The flat surface 40 is convenient to facilitate one particular manner of mounting.

In this embodiment, plug-in connectors are utilized including, without limitation, a female plug-in connector 46 at one lengthwise end 48 of the housing 24 and a male plug-in connector 50 at the opposite lengthwise end 52 of the housing 24.

As shown schematically in FIG. 10, the invention contemplates that the female and male electrical connectors, 46, 50, respectively, may take any form that allows them to be joined, preferably without the use of separate tools. For example, an arrangement is desirable that allows a simple press fit connection between the connectors 46, 50 to thereby electrically connect; a) the power source 28 to the electrical components 32 to effect energizing of a first fixture with at least one UV light source/bulb 26; and b) the components 32 on the first in line fixture to electrical components 32 on a separate fixture 22a to cause powering of one or more UV light sources 26 thereon.

In a preferred form, the female and male electrical connectors 46, 50 are military-grade connectors. In one form, the female and electrical connectors 46, 50 may respectively have supplementary mechanical/holding connectors 54, 56 that are engageable with each other to prevent separation of the female and male electrical connectors 46, 50. The schematic showing of the mechanical connectors is intended to encompass virtually any type of connectors that are used or could be devised to be joined, preferably without the need to use separate tools. As examples, the mechanical connectors 54, 56 may be complementarily threaded to be engaged by being turned relative to each other around an axis 58. A bayonet-type connection would also be usable. This type of push and turn connector is known.

As shown in association with the male electrical connector 50, a sleeve 60 is provided and knurled to facilitate grasping and both translational movement of the male electrical connector 50 and turning of the associated mechanical connector 56.

It is desirable that the power source 28 also have one of the female electrical connectors 46 so as to allow press fitting of a male electrical connector 50 to the power source 28. The power source 28 may also have an associated mechanical connector 54 to cooperate with the mechanical connector 56 associated with the male electrical connector 50.

Of course, the designation of "male" and "female" is arbitrary, as the only significant feature is the ability to make a press fit connection, one after the other, to serially electrically and mechanically connect the fixtures to the power source and elsewhere to each other.

In one preferred form, which is exemplary in nature only, the housing 24 has a length L of 17.5 inches, a width W of 5.75 inches, and a height H, combined with a lamp holder 62, of 3 inches.

In the depicted form, the main housing portion 34 and flanges 36, 38 are extrusion formed, as from aluminum. A U-shaped cover and ballast tray 64 is formed from stainless steel.

In a preferred form, at least one of the electrical connectors 46, 50 is connected to the housing 24 through a flexible whip 66. The whip 66 is preferably made from MC cable. The incorporation of a flexible whip 66 facilitates connection to the power source 28 and other fixtures 22 and further permits substantial flexibility in terms of how the fixtures 22 are placed and oriented relative to each other and positioned relative to other components making up the air handling unit 10. This allows accommodation to many different conditions as may be present in a particular air handling unit.

In this embodiment, the flexible whip 66 connects the male electrical connector 50 to the housing 24. The flexible whip 66 may have a range of different lengths, but it is preferable that it have a length of at least one foot, although this is not a requirement. This allows easy access to effect connection between the male connector 50 on the fixture 22 and the cooperating female electrical connector 46 associated with the power source 28. At the same time, this length permits the housing 24 to be reoriented relative to the power source 28 and other parts of the air handling unit within a range determined by the whip length.

In a preferred form, the flexible whip length is at least two feet and more preferably at least three feet, with the understanding that it could be virtually any length. It has been found that a three foot flexible whip length is desirable and allows the fixtures 22 to be made with the identical construction and conveniently serially joined so as to maximize exposure of the air within air handling units to UV light in an optimal fashion on a wide range of different commercially available products.

Figure 11:
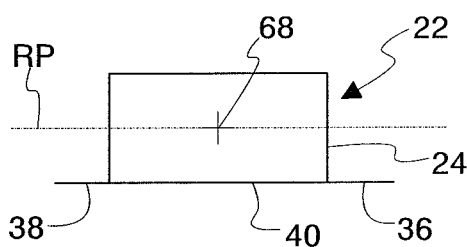
FIG. 11 is a schematic representation of an end view of the inventive fixture.

The flexibility of the inventive system will now be described in a somewhat schematic sense. In FIG. 11, an endwise view of the housing 24 is depicted. The housing has a lengthwise axis 68. With the flat mounting surface 40 placed on an underlying flat surface, the fixture 22 will be assumed to have a normal orientation, even though it can be mounted without a surface-to-surface connection relying on the mounting surface 40. In this normal orientation, a reference plane RP parallel to the plane of the mounting surface 40 extends through the lengthwise axis 68. FIG. 11 is provided to give a frame of reference in describing different orientations hereinbelow.

Figure 12:
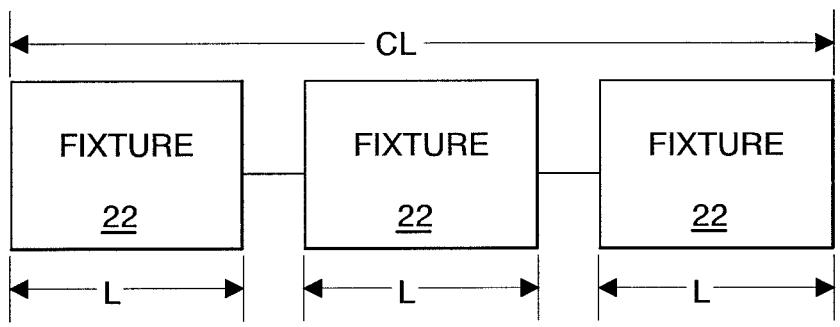
FIG. 12 is a schematic representation of three of the inventive fixtures electrically connected in series and arranged end-to-end.

In FIG. 12, the lengths L of each of the fixtures 22 are aligned, end-to-end, so as to produce a combined length CL. The reference planes RP for each fixture 22 may be coincident or non-coincident. They might be spaced and parallel or angled with respect to each other. While the lengthwise axes 68 are shown to be parallel, this is not required.

Figure 13:
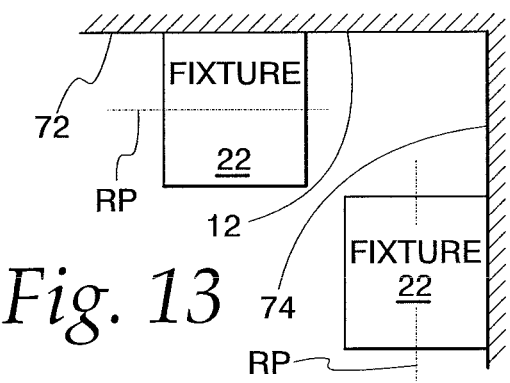
FIG. 13 is a schematic representation showing two of the inventive fixtures mounted so that corresponding reference planes, as shown in FIG. 11, and on the separate fixtures, are angled with respect to each other.

In FIG. 13, adjacent, joined fixtures 22 are mounted to transverse surfaces 72, 74 on an associated air handler housing 12 whereby the reference planes RP are angled, in this case so as to be substantially orthogonal to each other.

Figure 14:
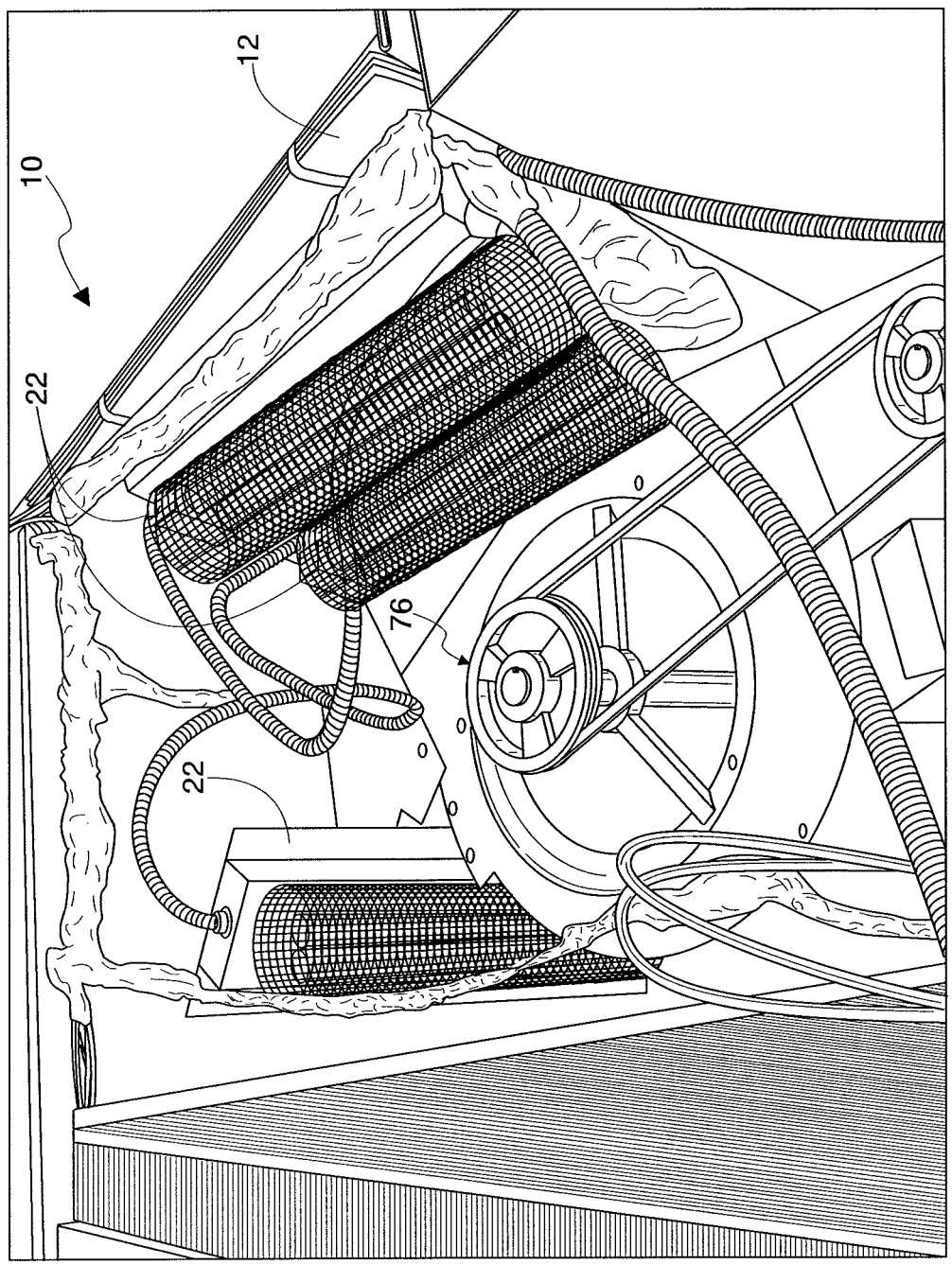
FIG. 14 is a perspective view of an exemplary air handling unit, with part thereof removed to show three of the inventive fixtures operatively installed.

FIG. 14 shows an actual installation wherein there are three fixtures 22 mounted to a housing of an air handling unit 10 at different locations on the housing in a somewhat random orientation around a fan unit 76.

The above are just representative examples of different relative positions for the various fixtures 22 contemplated, including spacing and relative orientation.

By making the flexible whip 66 long enough—as, for example, three feet—a manufacturer can offer a single fixture design with versatility substantial enough that it is adaptable to virtually any anticipated air handling unit size and construction.

Of course, the invention contemplates that flexible whips might be provided to connect each of the connectors 46, 50 to the same housing 24.

Figure 15:
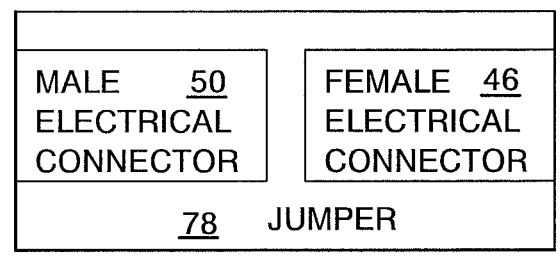
FIG. 15 is a schematic representation of a jumper used to connect between the power source and the inventive fixtures and/or between fixtures electrically connected in series.

In an alternative construction, as shown in FIG. 15, the flexible whip may be shortened or eliminated and a jumper 78 might be provided. A jumper has female and male electrical connectors 46, 50 at its opposite ends to allow connection between the power source 28 and fixtures 22 and between serially connected fixtures 22. The jumper 78 might be offered in a single length or with multiple lengths which can be selected by an installer to facilitate installation. The jumper 78 can be used to interconnect the fixtures 22 and connect a fixture 22 to the power source 28 to afford the same level of versatility in terms of orientation and spacing of the fixtures 22.

The invention makes possible a customized installation using the same basic fixture configuration to optimize exposure of air moving through an air handling unit to UV light of adequate strength. An installer can show up on a site with a plurality of potentially identical units and efficiently effect electrical and mechanical connections between the power source 28 and fixtures 22 with minimal requirements for tools. Most, and preferably all, of the connectors preferably can be hand joined.

Figure 16:
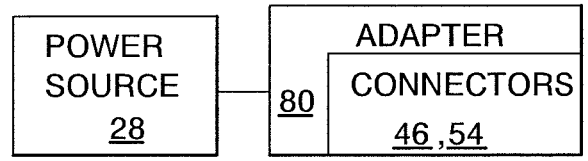
FIG. 16 is a schematic representation of an adaptor usable in association with a power source to facilitate electrical and mechanical connection of fixtures thereto.

Per FIG. 16, an adaptor 80 may be provided for the power source to incorporate the connectors 46, 54 as depicted in FIG. 7 to allow the electrical and mechanical connections between a fixture 22 and the power source 28, as described above.

The foregoing disclosure of specific embodiments is intended to be illustrative of the broad concepts comprehended by the invention.

The invention claimed is:

1. A method of treating air passing through an air handling unit, the air handling unit having a housing extending around an air handling space and a primary air treatment system that treats air as the air passes through the air handling unit between air inlet and outlet locations on the air handling unit, the method comprising the steps of:
   obtaining first and second fixtures each having a housing and a UV light source;
   strategically mounting the first and second fixtures to the air handling unit so that UV light from each of the UV light sources on the first and second fixtures treats air moving through the air handling unit with the UV light sources on the first and second fixtures energized; and
   serially electrically connecting the first and second fixtures to a power source to thereby cause the UV light sources on the first and second fixtures to be energized through the power source.

2. The method of treating air passing through an air handling unit according to claim 1 wherein the first and second fixtures each is elongate with a lengthwise axis.

3. The method of treating air passing through an air handling unit according to claim 2 wherein the first and second fixtures are mounted to the air handling unit housing so that the lengthwise axes of the housings of the first and second fixtures are substantially parallel.

4. The method of treating air passing through an air handling unit according to claim 2 wherein the first and second fixtures are mounted to the air handling unit housing so that the axes of the housings of the first and second fixtures are angled with respect to each other.

5. The method of treating air passing through an air handling unit according to claim 2 wherein the first and second fixtures are mounted to the air handling unit housing so that the axes of the housings of the first and second fixtures reside in corresponding planes that are not coincident and are not parallel.

6. The method of treating air passing through an air handling unit according to claim 2 wherein the first and second fixtures are mounted to the air handling unit housing so that the axes of the housings of the first and second fixtures reside in corresponding planes that are substantially orthogonal with respect to each other.

7. The method of treating air passing through an air handling unit according to claim 1 wherein the first fixture has electrical input and output connectors and one of the electrical input and output connectors is connected to the housing on the first fixture through a flexible whip, wherein the housings on the first and second fixtures are substantially the same and have an elongate shape with a lengthwise axis.

8. The method of treating air passing through an air handling unit according to claim 7 wherein the second fixture has an electrical input connector and the electrical output connector on the first fixture and electrical input connector are configured to be press connected, each to the other.

9. The method of treating air passing through an air handling unit according to claim 8 wherein there are cooperating holding connectors on the first and second fixtures that maintain the press connected electrical input connector on the second fixture and electrical output connector on the first fixture together.

10. The method of treating air passing through an air handling unit according to claim 9 wherein the cooperating holding connectors are configured to be engaged by moving the cooperating holding connectors relative to each other around an axis.

11. The method of treating air passing through an air handling unit according to claim 10 wherein the cooperating holding connectors are configured to be threadably engaged with each other.

12. The method of treating air passing through an air handling unit according to claim 7 wherein the flexible whip comprises an MC cable.

13. The method of treating air passing through an air handling unit according to claim 7 wherein the electrical input connector on the first fixture is connected to the housing through the flexible whip.

14. The method of treating air passing through an air handling unit according to claim 7 wherein the flexible whip has a length of at least one foot.

15. The method of treating air passing through an air handling unit according to claim 7 wherein the flexible whip has a length of at least 2 feet.

16. The method of treating air passing through an air handling unit according to claim 7 wherein the first and second fixtures are substantially the same.

17. The method of treating air passing through an air handling unit according to claim 1 wherein there are electrical and mechanical connectors associated with the power source that respectively cooperate with electrical and mechanical connectors on the first fixture, the electrical and mechanical connectors associated with the power source and on the first fixture configured to allow the electrical and mechanical connectors associated with the power source and on the first fixture to be releasably maintained together.

18. The method of treating air passing through an air handling unit according to claim 1 wherein the housings on the first and second fixtures are substantially the same and have an elongate shape with a lengthwise axis.

19. The method of treating air passing through an air handling unit according to claim 1 wherein the primary treatment system is configured to at least one of: a) change a temperature of: b) humidify; c) clean; and d) move air moving within the air handling space.

20. The method of treating air passing through an air handling unit according to claim 1 wherein the light source on each of the first and second fixtures comprises multiple bulbs.

21. The method of treating air passing through an air handling unit according to claim 1 further comprising a third fixture and the first, second, and third fixtures are serially connected, each to one of the power source and another of the fixtures.

\* \* \* \* \*

(12) EX PARTE REEXAMINATION CERTIFICATE (12053rd)

United States Patent
Skelton

(10) Number: US 10,806,818 C1
(45) Certificate Issued: May 10, 2022

(54) METHOD OF TREATING AIR PASSING THROUGH AN AIR HANDLING UNIT

(71) Applicant: PetAirapy LLC, St. Charles, IL (US)

(72) Inventor: David Skelton, Bartlett, TN (US)

(73) Assignee: PETAIRAPY LLC, St. Charles, IL (US)

Reexamination Request:
No. 90/014,919, Dec. 7, 2021

Reexamination Certificate for:
Patent No.: 10,806,818
Issued: Oct. 20, 2020
Appl. No.: 15/969,367
Filed: May 2, 2018

Related U.S. Application Data

(60) Provisional application No. 62/641,787, filed on Mar. 12, 2018.

(51) Int. Cl.
| | |
|---|---|
| *H01R 43/00* | (2006.01) |
| *A61L 9/20* | (2006.01) |
| *F21V 23/06* | (2006.01) |
| *F21V 33/00* | (2006.01) |
| *F21V 19/00* | (2006.01) |
| *F21V 23/02* | (2006.01) |

(52) U.S. Cl.
CPC ............ *F21V 23/06* (2013.01); *A61L 9/20* (2013.01); *F21V 19/00* (2013.01); *F21V 23/02* (2013.01); *F21V 33/0096* (2013.01); *A61L 2209/12* (2013.01); *Y10T 29/49169* (2015.01)

(58) Field of Classification Search
None
See application file for complete search history.

(56) References Cited

To view the complete listing of prior art documents cited during the proceeding for Reexamination Control Number 90/014,919, please refer to the USPTO's public Patent Application Information Retrieval (PAIR) system under the Display References tab.

*Primary Examiner* — Joseph A Kaufman

(57) ABSTRACT

A method of treating air passing through an air handling unit having a housing extending around an air handling space and a primary air treatment system that treats air as the air passes through the air handling unit between air inlet and outlet locations on the air handling unit. First and second fixtures are obtained, each having a housing and a UV light source. The first and second fixtures are strategically mounted to the air handling unit so that UV light from each of the UV light sources on the first and second fixtures treats air moving through the air handling unit with the UV light sources on the first and second fixtures energized. The first and second fixtures are serially electrically connected to a power source to thereby cause the UV light sources on the first and second fixtures to he energized through the power source.

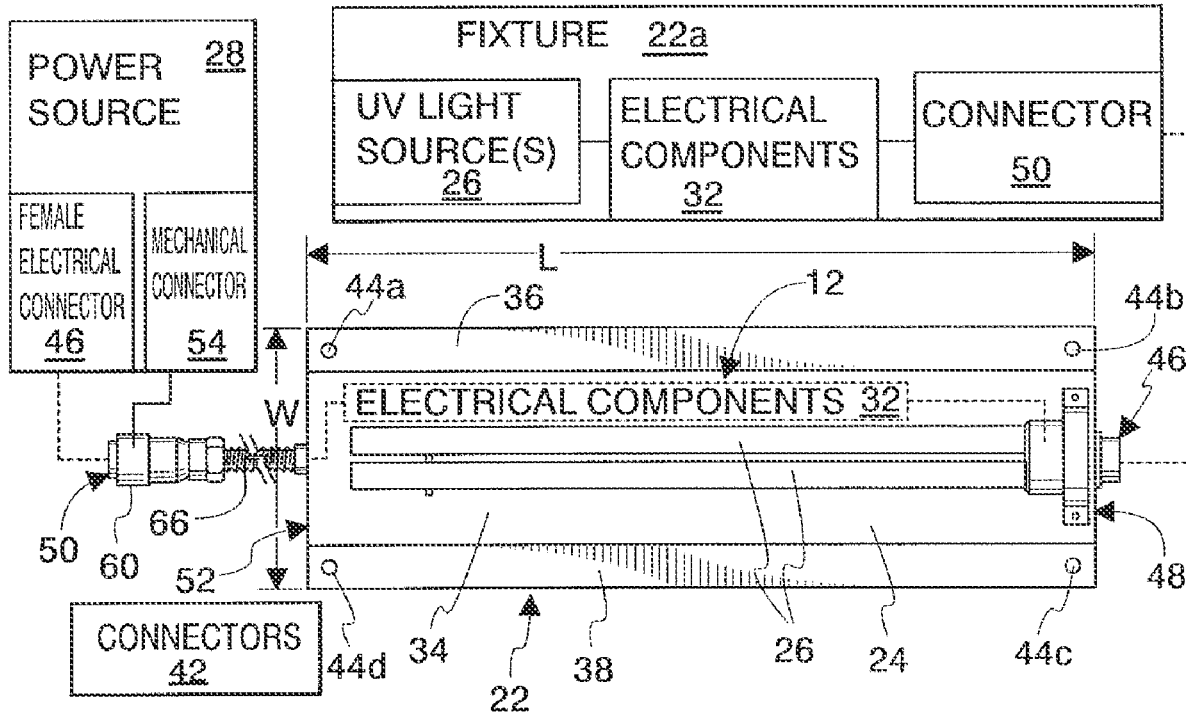

US 10,806,818 C1

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 3-21 is confirmed.

Claim 2 is determined to be patentable as amended.

New claims 22-27 are added and determined to be patentable.

2. The method of treating air passing through an air handling unit according to claim 1 wherein the *housing of each of the* first and second fixtures [each] is elongate with a lengthwise axis.

22. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing and a UV light source, each fixture housing including a ballast for energizing the UV light source;*

*strategically mounting the first and second fixtures to the air handling unit so that UV light from each of the UV light sources on the first and second fixtures treats air moving through the air handling unit with the UV light sources on the first and second fixtures energized; and*

*serially electrically connecting the first and second fixtures to a power source to thereby cause the UV light sources on the first and second fixtures to be energized through the power source.*

23. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing including a lamp holder and a UV light source, each fixture housing defining a space enclosing electrical components connected to the UV light source;*

*strategically mounting the first and second fixtures to the air handling unit so that UV light from each of the UV light sources on the first and second fixtures treats air moving through the air handling unit with the UV light sources on the first and second fixtures energized; and*

*serially electrically connecting the first and second fixtures to a power source to thereby cause the UV light sources on the first and second fixtures to be energized through the power source.*

24. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing and a UV light source, the first and second fixtures configured to be independently mounted, each from the other, in a plurality of different selected relative orientations;*

*strategically mounting the first and second fixtures to the air handling unit at different locations of the unit housing so that UV light from each of the UV light sources on the first and second fixtures treats air moving through the air handling unit with the UV light sources on the first and second fixtures energized; and*

*serially electrically connecting the first and second fixtures to a power source to thereby cause the UV light sources on the first and second fixtures to be energized through the power source.*

25. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing and a UV light source having a length and width, each fixture housing having a length and width, each greater than the length and width of a respective UV light source;*

*strategically mounting the first and second fixtures to the air handling unit so that UV light from each of the UV light sources on the first and second fixtures treats air moving through the air handling unit with the UV light sources on the first and second fixtures energized; and*

*serially electrically connecting the first and second fixtures to a power source to thereby cause the UV light sources on the first and second fixtures to be energized through the power source.*

26. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing and a UV light source having a length, each fixture housing having a length greater than the length of a respective UV light source;*

*strategically mounting the first and second fixtures to the air handling unit so that UV light from each of the UV light sources on the first and second fixtures treats air moving through the air handling unit with the UV light sources on the first and second fixtures energized; and*

*serially electrically connecting the first and second fixtures to a power source to thereby cause the UV light sources on the first and second fixtures to be energized through the power source.*

27. *A method of treating air passing through an air handling unit, the air handling unit having a housing extending around an air handling space and a primary air treatment system that treats air as the air passes through the air handling unit between air inlet and outlet locations on the air handling unit, the method comprising the steps of:*

*obtaining first and second fixtures each having a housing and a UV light source;*

*strategically mounting the first and second fixtures to the air handling unit housing with the fixture housings entirely within the air handling space so that UV light from each of the UV light sources on the first and second fixtures treats air moving through the air han-* dling unit with the UV light sources on the first and
second fixtures energized; and serially electrically connecting the first and second fixtures to a power source to thereby cause the UV light sources on the first and second fixtures to be energized through the power source.

\* \* \* \* \*